United States Patent
Ueda et al.

US 6,407,281 B1
Jun. 18, 2002

(54) PROCESS FOR PRODUCING OPTICALLY ACTIVE CYSTEINE DERIVATIVES

(75) Inventors: Yasuyoshi Ueda, Himeji; Hiroshi Murao; Takeshi Kondo, both of Takasago; Noboru Ueyama, Kobe; Hajime Manabe; Kenji Yoneda, both of Takasago; Akira Nishiyama, Kakogawa, all of (JP)

(73) Assignee: Kaneka Corporation, Osaka (JP)

(*) Notice: Subject to any disclaimer, the term of this patent is extended or adjusted under 35 U.S.C. 154(b) by 0 days.

(21) Appl. No.: 09/600,253
(22) PCT Filed: Jan. 13, 1999
(86) PCT No.: PCT/JP99/00074
§ 371 (c)(1),
(2), (4) Date: Aug. 25, 2000
(87) PCT Pub. No.: WO99/36399
PCT Pub. Date: Jul. 22, 1999

(30) Foreign Application Priority Data

Jan. 13, 1998 (JP) ............................................ 10-017744
May 28, 1998 (JP) ............................................ 10-146771

(51) Int. Cl.$^7$ ...................... C07C 321/00; C07C 323/00
(52) U.S. Cl. ........................ 560/17; 560/152; 560/153; 560/147; 560/9
(58) Field of Search ...................... 562/9, 426; 560/147, 560/152, 17, 153

(56) References Cited

U.S. PATENT DOCUMENTS 4,676,989 A * 6/1987 Barrett et al.
5,219,731 A * 6/1993 Ueda et al.
5,262,436 A * 11/1993 Haslanger et al.
5,874,468 A * 2/1999 Atlas et al.

OTHER PUBLICATIONS

Brtnik et al. (1986). Amino acids and peptides. Collection Czechoslavak Chem. Commun. 51 (7), pp. 1532–1541.*
Derwent abstract (Acc No 1983–48865k) of SU 941353B. Preparation of butyloxy–carbonyl–cysteinyl–cysteine derivative by introducing hydroxymethyl–pyrrolidone group into cysteine hydrochlorde, acylating, condensing with cysteine compound with iodine.*

* cited by examiner

Primary Examiner—Paul J. Killos
Assistant Examiner—Mahreen Chaudhry
(74) Attorney, Agent, or Firm—Connolly Bove Lodge & Hutz LLP

(57) ABSTRACT

A process for producing optically active cysteine derivatives with high optical purity and good quality which is economically advantageous and is high in productivity even on a commercial scale is provided.

A process for producing an optically active cysteine derivative which comprises synthesizing a D-form or L-form optically active cysteine derivative of the general formula (2) shown below ($R^1$ represents an amino-protecting group of the urethane or acyl type, $R^0$ represents a hydrogen atom or, taken together with $R^1$, an amino-protecting group, $R^2$ represents an alkyl, aryl or aralkyl group, $R^3$ represents a univalent organic group and * represents the position of an asymmetric carbon) by reacting the corresponding D-form or L-form optically active amino acid derivative of the general formula (1) shown below with an alcohol of the general formula (3) shown below and a strong acid and/or a thionyl halide and recovering the above cysteine derivative (2) from the reaction mixture, the procedural series from reaction to recovery being carried out under conditions such that the medium contacting the above optically active cysteine derivative (2) is within the range from acidic to weakly basic to thereby recover the above cysteine derivative (2) from the reaction mixture while suppressing the decomposition and racemization thereof.

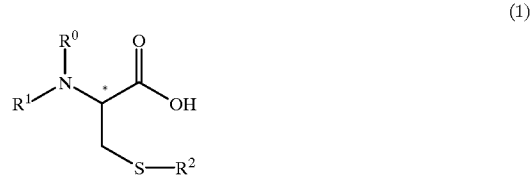

(1)

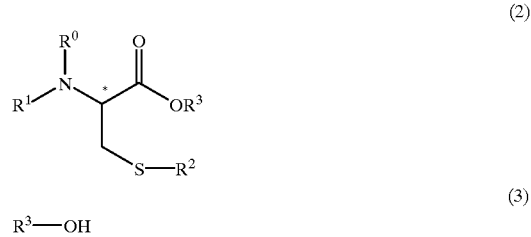

(2)

$R^3$—OH (3)

21 Claims, No Drawings

PROCESS FOR PRODUCING OPTICALLY ACTIVE CYSTEINE DERIVATIVES

TECHNICAL FIELD

The present invention relates to a process for producing a D-form or L-form optically active cysteine derivative represented by the general formula (2) (hereinafter, such derivatives are also referred to as "cysteine derivatives (2)"):

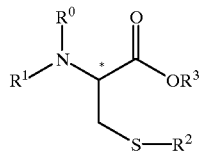

(2)

wherein $R^1$ represents an amino-protecting group of the urethane or acyl type, $R^0$ represents a hydrogen atom or, taken together with the above $R^1$, an amino-protecting group, $R^2$ represents a univalent organic group selected from the group consisting of a substituted or unsubstituted alkyl group containing 1 to 7 carbon atoms, a substituted or unsubstituted aryl group containing 6 to 10 carbon atoms and a substituted or unsubstituted aralkyl group containing 7 to 10 carbon atoms, $R^3$ represents a univalent organic group capable of functioning as an ester-type carboxyl-protecting group by its being included in the structure represented by —$COOR^3$ and * represents the position of an asymmetric carbon atom.

BACKGROUND ART

The cysteine derivatives (2), particularly in L form, which are obtainable by the present invention are compounds of importance as starting materials for the production of intermediates of HIV protease inhibitors. For example, said derivatives are useful as starting materials in the reaction scheme shown below, as described in WO 96/23756 and EP 604185 A1, for instance.

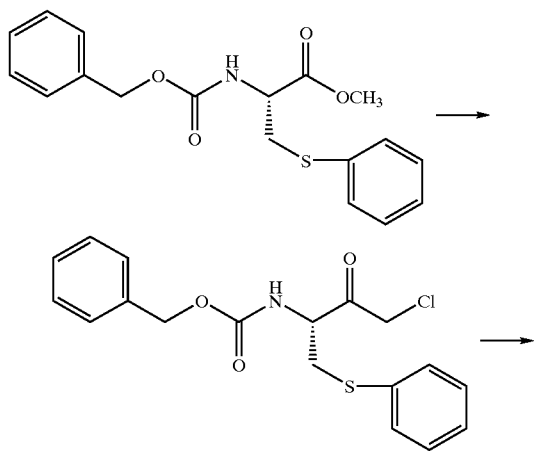

-continued

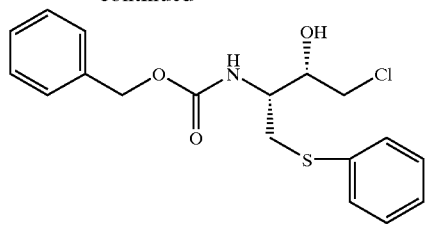

A production technology for the above cysteine derivatives (2) which is so far known in the art comprises introducing an $R^2S$ group ($R^2$ being as defined above) into a corresponding compound whose amino and carboxyl groups are protected.

Referring to this technology, a method is known which comprises converting the hydroxyl group of a serine derivative to a leaving group and then carrying out the substitution reaction [Tetrahedron Lett., vol. 28, p. 6069 (1987); ibid., vol. 34, p. 6607 (1993); EP 604185 A1].

In this way, the hydroxyl group of a serine derivative is converted to a sulfonyloxy group, followed by substitution reaction with a thiol derivative in an aprotic solvent. However, as a result of investigations made by the present inventors, it was revealed that the yield of the desired cysteine derivative (2) is not always high and that there are other problems; the quality is poor and, in particular, the optical purity decreases.

Further, there is no detailed description of the method of isolation of the desired cysteine derivative (2), and the above method cannot be said to be a production technology leading to good yields.

Thus, any method of producing those cysteine derivatives (2), which are important as raw materials for the production of intermediates of HIV protease inhibitors, has not been established as yet.

In view of the current state of the art as mentioned above, the primary object of the present invention is to provide a process for producing cysteine derivatives (2) which is economically advantageous and insures high productivity even on a commercial scale, together with high optical purity and good quality.

DISCLOSURE OF INVENTION

Investigations made by the present inventors revealed that the above cysteine derivatives (2) are unexpectedly unstable and, in particular, highly basic conditions bring about such undesirable events as racemization and decreases in yield. This is presumably because abstraction of the hydrogen atom at position a to the carbonyl group or E2 elimination is caused by high basicity, leading to formation of a dehydroalanine derivative as a byproduct, and, on the other hand, the elimination product thiol derivative reacts with the byproduct dehydroalanine derivative in the manner of Michael addition, as shown by the following reaction formula:

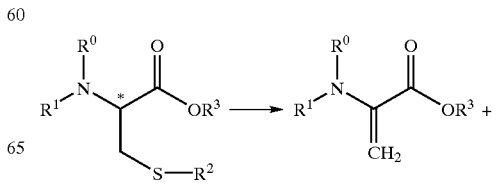

-continued

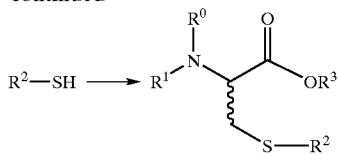

It is therefore believed that it is not easy to suppress decomposition or racemization of the above cysteine derivatives (2) when such a prior art technology as the one mentioned above, that generally requires highly basic reaction conditions, is used.

Based on the above finding, the present inventors made intensive investigations in search of a process for allowing the reaction to proceed smoothly and recovering the above cysteine derivatives (2) while suppressing the decomposition and racemization of the cysteine derivatives (2) and, as a result, found out a process favorable for carrying out the procedural series from reaction to recovery under acidic to weakly basic conditions while avoiding highly basic conditions.

Thus, the present invention is related to a process for producing the above optically active cysteine derivative (2) which comprises reacting a D-form or L-form optically active amino acid derivative represented by the general formula (1) (hereinafter also referred to as "amino acid derivative (1)"):

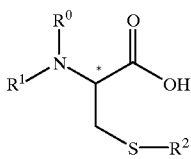

(1)

wherein $R^0$, $R^1$, $R^2$ and * are as defined above, with an alcohol represented by the general formula (3) (hereinafter also referred to as "alcohol (3)"):

$$R^3OH \quad (3)$$

wherein $R^3$ is as defined above, and a strong acid and/or a thionyl halide to synthesize a D-form or L-form optically active cysteine derivative represented by the above general formula (2)

and recovering the above optically active cysteine derivative (2) from the reaction mixture, the procedural series from reaction to recovery being carried out under a condition such that the medium contacting the above optically active cysteine derivative (2) is within the range from acidic to weakly basic to thereby recover the above optically active cysteine derivative (2) from the reaction mixture while suppressing the decomposition and racemization thereof.

In the following, the present invention is described in detail.

In the production process of the present invention, by carrying out the reaction using a strong acid and/or a thionyl halide, the reaction system can be maintained under acidic conditions under which the decomposition and racemization of the above cysteine derivative (2) can be completely inhibited. Thus, the reaction system is maintained under acidic conditions throughout the process, or the conditions therein favorably shift to acidic conditions as the reaction proceeds, namely with the formation of the cysteine derivative (2).

Referring to the above general formula (1) or (2), $R^1$ represents a urethane-type or acyl-type amino-protecting group. The urethane-type or acyl-type protective group is not particularly restricted but may be any one having an amino-protecting effect. For example, it can be selected from among those protective groups described in Protective Groups in Organic Synthesis, 2nd edition, published by John Wiley & Sons (1991).

Under such reaction conditions as mentioned above, urethane-type and acyl-type protective groups are judiciously used for masking the basicity of the amino group. Among them, urethane-type protective groups such as aralkyloxycarbonyl groups and lower alkyloxycarbonyl groups are preferred from the viewpoint of ease of handling, inexpensiveness and convenience in substrate compound synthesis, among others. In particular, benzyloxycarbonyl, tert-butoxycarbonyl, methoxycarbonyl and ethoxycarbonyl are preferred, and benzyloxycarbonyl is more preferred.

The above symbol $R^0$ usually represents a hydrogen atom. When the above amino-protecting group is a phthaloyl group or the like, however, it, together with the above $R^1$, represents an amino-protecting group.

The above $R^2$ represents an alkyl group containing 1 to 7 carbon atoms, an aryl group containing 6 to 10 carbon atoms or an aralkyl group containing 7 to 10 carbon atoms. These groups may optionally be substituted according to need. Preferred as $R^2$ is phenyl, however.

The amino acid derivatives (1) to which the process of the present invention is favorably applicable are those S-phenylcysteines ($R^2$=phenyl) whose amino group is protected by a urethane-type or acyl-type protective group. Among them, those S-phenylcysteines ($R^2$=phenyl) whose amino group is protected by a urethane-type protective group are more preferred, and that S-phenylcysteines ($R^2$=phenyl) whose amino group is protected by benzyloxycarbonyl, namely D-form or L-form N-benzyloxycarbonyl-S-phenylcysteine ($R^0$=hydrogen, $R^1$=benzyloxycarbonyl, $R^2$=phenyl), is particularly preferred.

Since, as mentioned above, the $R^2S$ group tends to undergoing elimination and, when $R^2$ is an aryl group containing 6 to 10 carbon atoms, in particular phenyl, the tendency toward elimination generally increases. Even in such cases, the process of the present invention can be used very favorably.

Referring to the above general formula (2) or (3), $R^3$ represents a univalent organic group capable of functioning as an ester-type carboxyl-protecting group through its being included in the structure represented by $-COOR^3$, as is evident from the above general formula (2). The above univalent organic group is not particularly restricted but may be any one having a carboxyl-protecting effect. For example, it can be selected from among those protective groups described in Protective Groups in Organic Synthesis, 2nd edition, published by John Wiley & Sons (1991). Among them, lower alkyl, benzyl, substituted benzyl and like groups are preferred, lower alkyl groups containing 1 to 4 carbon atoms are more preferred, and methyl is most preferred.

The term "protecting" as used herein with reference to the above $R^1$ and $R^3$ means that the relevant functional group is in a form modified so that no undesirable side reactions can occur.

The amount of the above alcohol (3) is not particularly restricted but the alcohol may be used in an amount not less than about 1 equivalent per equivalent of the above amino acid derivative (1). Generally, however, the above reaction is carried out using the above alcohol (3) in excess relative to the above amino acid derivative (1). Preferably, the reaction is carried out using a large excess of the above alcohol (3) as a reaction solvent.

The strong acid to be used according to the invention is not particularly restricted but includes, among others, inorganic acids such as sulfuric acid and hydrochloric acid; and organic acids such as p-toluenesulfonic acid, benzenesulfonic acid and methanesulfonic acid.

Preferred as the above strong acid are those showing a pKa of not more than 2.0, more preferably not more than 1.0, in aqueous solutions. When the above strong acid is a polybasic acid such as sulfuric acid, the above pKa indicates the value at the first stage of dissociation at which that value is minimal. It is to be noted that a compound simultaneously having an acidic group and a basic group such as an amino group, for example an amino acid, even if it has an acidic group showing such a small pKa value, is distinguished from the strong acid to be used in the practice of the present invention, since it, as the whole molecule, does not show strong acidity.

The amount of the above strong acid is not particularly restricted but, preferably, the strong acid is used in an amount not smaller than the catalytic amount, more preferably 0.01 to 0.1 equivalent, relative to the above amino acid derivative (1), if necessary in a still larger amount.

When hydrogen chloride is used as the above strong acid, it is generally used by blowing into the reaction solvent. For example, it is blown through the above alcohol (3), which also serves as a reaction solvent, to an extent such that the solvent is saturated with the same.

The thionyl halide to be used in the present invention is not particularly restricted but thionyl chloride is preferred from the viewpoint of ease of handling and inexpensiveness, for instance.

The amount of the above thionyl halide is not particularly restricted but, generally, it is used preferably in an amount of not less than about 1 equivalent, more preferably within the range of 1 to 5 equivalents, relative to each equivalent of the above amino acid derivative (1). Most preferably, it is used in an amount of about 1 equivalent or a slightly larger than 1 equivalent.

In carrying out the reaction according to the present invention, the three materials, namely the above amino acid derivative (1), the above alcohol (3) and the above strong acid or thionyl halide are generally brought into contact with one another all at once. When, however, the above thionyl halide is used, it is also possible to react the above thionyl halide with the above alcohol (3) in advance and then react this mixture with the above amino acid derivative (1). Generally, either one of the above strong acid and the above thionyl halide is used. It is also possible, however, to use both the above strong acid and thionyl halide simultaneously.

The reaction temperature for the above reaction is not restricted. Generally, however, it is within the range of from the solidification point of the reaction mixture to about 100° C., preferably within the range of −20° C. to 80° C.

The time required for going through the above reaction may vary depending on the species and amounts of the above amino acid derivative (1), alcohol (3) and strong acid or thionyl halide as well as on the reaction temperature. Generally, however, it is 1 to 120 hours. In particular, it is preferred that the reaction be caused to proceed almost quantitatively within 20 hours.

The reaction solvent to be used in the above reaction is not particularly restricted. Generally, the above alcohol (3) is used also as the reaction solvent. For minimizing the amount of the alcohol (3), an aromatic hydrocarbon, an ether or the like may also be used as the reaction solvent. From the viewpoint, among others, of ease of removal, by azeotropic distillation, of the byproduct water formed in small amounts, a solvent immiscible with water and facilitating the removal of water by distillation is preferred among others, and a solvent capable of forming an azeotrope with water is more preferred. As such solvent, there may be mentioned aromatic hydrocarbons and, in particular, 6-membered aromatic hydrocarbons containing 6 to 8 carbon atoms are more preferred, and a most preferred solvent is toluene.

The reaction mixture after completion of the reaction effected according to the present invention contains not only the desired compound, namely the above cysteine derivative (2), but also the above strong acid and/or the hydrogen halide and sulfur dioxide formed as byproducts and dissolved therein when the above thionyl halide is used; thus, it is in a state containing a very strongly acidic substance or substances.

The above cysteine derivative (2) is favorably protected against decomposition or racemization under acidic conditions and, therefore, such strongly acidic substances need not always be removed. If desired, however, they may be eliminated by evaporation or neutralization. Elimination by neutralization is preferred and, when a thionyl halide is used, combined use of removal by evaporation (e.g. degassing under reduced pressure) and elimination by neutralization is judicious.

In the practice of the present invention, the removal of the above strong acid and/or the byproduct hydrogen halide and sulfur dioxide is conducted under acidic to weakly basic conditions so that the above cysteine derivative (2) may be prevented from being decomposed or racemized, as mentioned above. When said conditions are defined in terms of pH, the elimination is carried out generally at a pH not higher than 10, preferably at a pH not higher than 9, more preferably at a pH of 3 to 8 (pH 5.5±2.5), although the conditions may vary depending on the time for the operation.

The above-mentioned elimination by neutralization is effected by bringing the reaction mixture after completion of the reaction into contact with a base. In this case, although the base itself maybe contacted with the above reaction mixture, it is a preferred general practice to dissolve or suspend the base in water or an organic solvent and bring the solution or suspension into contact with the above reaction mixture.

The base to be used in the above neutralization is not particularly restricted but includes, among others, amines such as triethylamine and diisopropylamine; alkali metal hydroxides such as sodium hydroxide, potassium hydroxide and lithium hydroxide; alkaline earth metal hydroxides such as calcium hydroxide and magnesium hydroxide; carbonate salts such as sodium carbonate and potassium carbonate; and hydrogen carbonate salts such as sodium hydrogen carbonate and potassium hydrogen carbonate. From the viewpoint of operability, carbonate or hydrogen carbonate salts are preferred among others, and hydrogen carbonate salts are more preferred. Sodium hydrogen carbonate is still more preferred.

Meanwhile, with those amino acid derivatives (1) whose amino group is protected by benzyloxycarbonyl, for example N-benzyloxycarbonyl-S-phenylcysteine ($R^0$=hydrogen, $R^1$=benzyloxycarbonyl, $R^2$=phenyl), there is a tendency toward contamination with a structurally analogous impurity, namely a compound represented by the general formula (4):

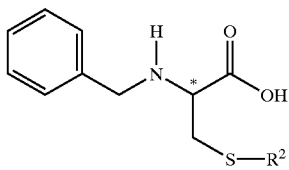

(4)

wherein $R^2$ and * are as defined above, for example N-benzyl-S-phenylcysteine, differing from the corresponding derivative (1) only in that the above benzyloxycarbonyl group is replaced by a benzyl group and originating from the raw material benzyloxycarbonyl halide and/or the process of their synthesis (e.g. Schotten-Baumann reaction). It is difficult to completely prevent the formation of this structurally analogous impurity (4) and, further, it is very difficult to remove said contaminant for purification even when the amount thereof is small (e.g. 1% or less, or 0.5% or less).

As is well known in the art, a structurally analogous impurity, because of its similarity in structure, behaves in the same manner as the substrate compound or desired final compound in the procedural process from reaction to after-treatment and as a result tend to exist as a contaminant in the final product. When the final product is a medicinal, the presence of a trace amount of a structurally analogous impurity may cause a very serious problem in some cases.

According to the process of the present invention, it is possible to cause the structurally analogous impurity (4) existing in the amino acid derivative (1) whose amino group is protected with a benzyloxycarbonyl group to remain substantially unreacted. This is a very great advantage of the process of the present invention.

Specifically, when N-benzyloxycarbonyl-S-phenylcysteine methyl ester ($R^0$=hydrogen, $R^1$=benzyloxycarbonyl, $R^2$=phenyl, $R^3$=methyl), for instance, is to be produced as the above cysteine derivative (2) using N-benzyloxycarbonyl-S-phenylcysteine ($R^0$=hydrogen, $R^1$=benzyloxycarbonyl, $R^2$=phenyl) as the amino acid derivative (1), it is possible to cause the contaminant N-benzyl-S-phenylcysteine existing as an impurity in the above amino acid derivative (1) to remain substantially unreacted even after completion of the reaction by using a thionyl halide in an amount of about 1 equivalent or slightly larger than 1 equivalent relative to the above amino acid derivative (1) or a strong acid in an amount of 0.01 to 0.1 equivalent, as mentioned herein above. Therefore, by making use of the large difference in solubility in a solvent, for instance, between the desired product N-benzyloxycarbonyl-S-phenylcysteine methyl ester and the remaining impurity N-benzyl-S-phenylcysteine, it is possible to readily remove this impurity from the reaction mixture by carrying out such a general separation procedure as filtration and/or extraction and washing after completion of the reaction.

A method of recovering the desired product of the present invention, namely the cysteine derivative (2), from the reaction mixture is now described. The reaction mixture so referred to herein means the reaction mixture after completion of the reaction.

In the production process of the present invention, the desired compound, namely the cysteine derivative (2), may be recovered from the reaction mixture by a separational procedure comprising extraction and washing or it can be recovered without any extraction procedure. Of course, these recovery procedures are conducted under acidic to weakly basic conditions. When the conditions are defined in terms of pH, the pH is generally not higher than 10, preferably not higher than 9, more preferably not higher than 8.

The method of recovering the above cysteine derivative (2) from the reaction mixture by a separational procedure comprising extraction and washing is a method of recovery which comprises carrying out extraction with an organic solvent, separating the organic extract phase, and carrying out the concentration or crystallization. Preferred modes of this method are described below in detail. It is more advantageous to use these preferred modes in combination.

In the above extraction step, the reaction mixture as such may be blended with an extraction solvent. For preventing the remaining reaction solvent from adversely affecting the procedure for separating the organic phase from the aqueous phase, however, blending after reducing the content of the above reaction solvent is preferred. In this case, it is more preferred to replace the reaction solvent with the extraction solvent. In cases where the above alcohol (3), in particular a lower alcohol containing 1 to 4 carbon atoms, which is particularly high in affinity for water, remains in a large amount in the reaction mixture, it is judicious to conduct the separation procedure after lowering the alcohol content in the system by recovering the alcohol, for instance.

According to the prior art, the separation of the cysteine derivative (2) by extraction and washing has drawbacks, for example it requires a large amount of an organic solvent, making it difficult to employ such method of separation on an industrial scale where the productivity is an important factor. However, investigations made by the present inventors revealed that when the procedure mentioned below is employed, such separation can be carried out in a simple and efficient manner and can give high yields.

The difficulty in phase separation is generally caused by the formation of an emulsified intermediate phase between the organic and aqueous phases and the slow rate of disappearance of that intermediate phase. It was found, however, that the difficulty in phase separation in the steps of extraction and washing of the desired product of the present invention, namely the cysteine derivative (2) is not due to that generally known formation of an emulsified intermediate phase but is due to failure in forming separable two layers, the upper and lower layers, because, in spite of separation into two phases, an organic and an aqueous phase, a large number of droplets consisting of one phase remain dispersed in the other phase but will not coalesce.

In the practice of the present invention, it is preferred that, in the step of organic-aqueous phase separation, the mixture composed of an organic phase containing the above cysteine derivative (2) and an aqueous phase be supplemented with an inorganic salt and/or subjected to warming treatment to thereby successfully attain phase separation into the organic and aqueous phases, followed by recovering the organic phase containing the cysteine derivative (2). In this case, the addition of an inorganic salt is more preferably combined with the warming treatment. For example, when an inorganic salt such as sodium chloride and sodium sulfate is caused to coexist and at the same time the system is maintained in a warmed condition, two layers, the upper and lower layers, can be formed very easily and, at the same time, separation can be realized efficiently without using the organic solvent in a large amount.

More specifically, when the above cysteine derivative (2) is N-benzyloxycarbonyl-S-phenyl-L-cysteine methyl ester ($R^0$=hydrogen atom, $R^1$=benzyloxycarbonyl, $R^2$=phenyl, $R^3$=methyl) and the extraction is carried out using toluene, the mixture is warmed at a temperature of not lower than about 40° C. in the presence of sodium chloride in an amount such that its concentration in water amounts to about 5% by weight to the saturated concentration, whereby two layers composed of the upper and lower layers can be formed very easily.

The extraction solvent to be used in the above method of separation is not particularly restricted but includes, among others, aromatic hydrocarbons such as toluene; acetate esters such as ethyl acetate; and ethers such as methyl tert-butyl ether. In particular, the use of at least one of toluene and ethyl acetate is preferred.

For removing, by causing it to transfer to the aqueous phase in separating the organic phase from the aqueous phase, the above compound (4) which has a benzyl group introduced onto the amino group such as N-benzyl-S-phenyl-L-cysteine and remains unreacted as an impurity, it is judicious to add an inorganic salt and/or perform warming treatment, as mentioned above, and carry out the phase separation procedure including extraction and washing, if necessary repeatedly, under acidic conditions, for example at a pH of not higher than 3, ordinary not higher than 2, preferably not higher than 1, more preferably in the vicinity of pH 0 or less than it. According to need, it is also possible to cause a water-miscible organic solvent (e.g. a monohydric alcohol containing 1 to 4 carbon atoms, for example methanol) to be contained in the aqueous phase.

In recovering the above cysteine derivative (2) from the thus-separated organic phase containing the cysteine derivative (2), the method mentioned below can be employed by which the recovery can be accomplished in a simple manner with high yields even in commercial scale production where the productivity is of importance.

The present inventors found that, in distilling off the solvent from the organic phase containing the above cysteine derivative (2), it is important to select the operational conditions taking into consideration the melting temperature of the above cysteine derivative (2) or the melting temperature of the concentrate mainly comprising the above cysteine derivative (2) and the temperature for distilling off the solvent. Namely, it was unexpectedly found that by distilling off the above solvent at a temperature above such a melting temperature (where there is a melting temperature range, above the temperature at which the melting begins), it is possible to obtain the above cysteine derivative (2) as an oil very low in viscosity and easy to handle.

When the above cysteine derivative (2) is N-benzyloxycarbonyl-S-phenyl-L-cysteine methyl ester ($R^0$=hydrogen atom, $R^1$=benzyloxycarbonyl, $R^2$=phenyl, $R^3$=methyl), for instance, the N-benzyloxycarbonyl-S-phenyl-L-cysteine methyl ester can be recovered as an oil, by distilling off the toluene at about 60 to 70° C. or above, from the organic phase obtained by toluene extraction, washing and phase separation.

The above oily cysteine derivative (2) may be recovered in the form of a solution by adding a solvent, if necessary. When tetrahydrofuran, for instance, is added to the above oily product, the derivative (2) can be recovered in the form of a tetrahydrofuran solution. By doing so, a solvent differing much in boiling point, for example toluene, which is a high-boiling solvent, can be exchanged for tetrahydrofuran, which is a low-boiling solvent, very efficiently.

When the above solvent removal by distillation is carried out at a lower temperature, the above cysteine derivative (2) solidifies during distilling off the solvent, increasing the load on stirring or causing insufficient stirring, which results in incomplete solvent removal by distillation. In this case, the derivative (2) can be obtained in the form of a solution only by a complicated procedure comprising repeating the procedure for solvent removal by distillation while supplementing the solvent. For example, the replacing a high-boiling toluene solution to a low-boiling tetrahydrofuran solution is very inefficient and a stabilizer such as BHT coexisting in tetrahydrofuran is concentrated to a high level in the solution and may sometimes produce unfavorable affects when used in the next step.

An alternative method of recovering the above cysteine derivative (2) from the above organic phase resulting from phase separation comprises causing the above cysteine derivative (2) to precipitate out from the organic phase containing the cysteine derivative (2) and an organic solvent miscible with an aliphatic hydrocarbon or from a concentrate derived from said organic phase by using such an aliphatic hydrocarbon as a poor solvent, if necessary with cooling, followed by recovering the precipitate, for example a crystallization procedure.

When, for example, the cysteine derivative (2) is one in which $R^0$ is a hydrogen atom, $R^1$ is a urethane-type protective group, $R^2$ is a phenyl group and $R^3$ is an alkyl group containing 1 to 4 carbon atoms, it is possible to favorably crystallize out the above cysteine derivative (2) from its solution in an organic solvent miscible with an aliphatic hydrocarbon by using such an aliphatic hydrocarbon as a poor solvent, if necessary with cooling and/or concentration.

The organic solvent miscible with an aliphatic hydrocarbon is not particularly restricted but includes aromatic hydrocarbons such as toluene; acetate esters such as ethyl acetate and isopropyl acetate; and ethers such as methyl tert-butyl ether. Toluene is particularly preferred among the aromatic hydrocarbons, ethyl acetate among the acetate esters, and methyl tert-butyl ether among the ethers. At least one of these solvents is preferably used. The aliphatic hydrocarbon to be used as a poor solvent in combination with the above organic solvent is not particularly restricted but may be, for example, hexane, heptane, methylcyclohexane or the like. Hexane is preferred, however.

Generally, it is convenient to admix the above poor solvent with an organic solvent solution containing the above cysteine derivative (2). For controlling the amount of the cysteine derivative remaining dissolved in the step of crystal precipitation, it is also possible, if necessary, to cool the mixture, or to concentrate the above solution by distilling off under reduced pressure an arbitrary amount of the solvent constituting the above solution, followed by admixing with the poor solvent. It is judicious to adjust the amount of the poor solvent to be added, the amount of the above solvent to be distilled off, and/or the extent of cooling, as necessary, depending on the solvent species constituting the above solution and the amount thereof.

The amount of the above poor solvent is not particularly restricted. From the viewpoint of improved recovery rate and improved operability, among others, it is generally about 10% by weight or more, preferably about 20% by weight or more, more preferably about 30% by weight or more, based on the total weight of the solution, for instance.

The above method of crystallization can be carried out by combinedly using generally known crystallization procedures such as crystallization with cooling or by concentration.

Generally, it is preferred that the concentration in the step of crystallization be not more than about 30% (w/v), more preferably not more than about 20% (w/v), as the weight of the cysteine derivative (2) relative to the total volume of the solution as resulting from adjusting the amount of the poor solvent to be added and the amount of the solvent to be distilled off, among others, within the ranges which allow the solution to maintain its fluidity.

The temperature for the above precipitation is not restricted but generally is from the solidifying temperature to about 60° C. For producing a crystallization mixture (slurry) having good properties, it is judicious to allow the crystallization to proceed slowly, for example by slow cooling or slow addition of the above poor solvent.

For preventing the cysteine derivative (2) from being decomposed or racemized, the above method of crystallization is preferably carried out under acidic to weakly basic conditions after removing the unnecessary base component.

In the above method of crystallization, the cysteine derivative is precipitated as crystals from a solution of the cysteine derivative (2) in an organic solvent miscible with an aliphatic hydrocarbon using the aliphatic hydrocarbon as a poor solvent, if necessary with cooling and/or carrying out concentration, while removing the impurity mixed in the cysteine derivative therefrom.

The above-mentioned method of crystallization is applicable also to the crystallization of the product obtained by a process other than the production process of the present invention, for example by the process comprising converting the hydroxyl group of a serine derivative to a leaving group and then carrying out the substitution reaction [Tetrahedron Lett., vol. 28, page 6069 (1987); ibid., vol. 34, page 6607 (1993); EP 604185 A1; WO 98/30538]. Particularly when a low grade of the cysteine derivative (2) containing impurities such as the optical isomer of the cysteine derivative (2) and a dehydroalanine derivative is treated by the above-mentioned method of crystallization, said dehydroalanine derivative being represented by the general formula (5):

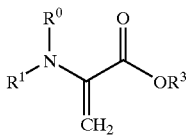

(5)

wherein $R^0$ represents a hydrogen atom, $R^1$ represents a urethane type amino-protecting group and $R^3$ represents an alkyl group containing 1 to 4 carbon atoms,
and being hardly formed as byproducts in the production process of the present invention,
  the impurities mentioned above can be removed efficiently, hence the above method of crystallization is effective also as a method of purifying the cysteine derivative (2). For example, the content of the impurity optical isomer can be reduced to 2% or less, preferably to 1% or less, and the dehydroalanine derivative (5) can be almost completely removed.

For the effects of the above method of purification to be produced to its maximum, when the cysteine derivative (2) contains its optical isomer as an impurity, it is judicious to adjust the crystallization conditions such as species of the solvent, the mixing ratio therebetween and the recovery temperature in the step of crystallization so that the relative equilibrium solubility (equilibrium ratio between the amounts dissolved) in the crystallization mixture between the optically active cysteine derivative (2), which is the desired product, and its optical isomer may become lower than the optical purity of the cysteine derivative before crystallization, to thereby cause preferential crystallization of the desired optically active cysteine derivative (2), which exists in excess, while efficiently removing the impurity optical isomer into the mother liquor. By this measure, it is possible to obtain the optically active cysteine derivative (2) with a percent existence of the desired optical isomer of not less than 98%, preferably not less than 99%.

In other words, the relative solubility in the solution between the optically active cysteine derivative (2) and its optical isomer has a constant value (namely, there is an equilibrium ratio between the amounts dissolved) depending on the crystallization conditions selected, such as the solvent species and the mixing ratio between the solvents constituting the mixed solvent, independently of the optical purity of the cysteine derivative used in the crystallization step, so that when the optical purity of the cysteine derivative used in the crystallization step is higher than the equilibrium ratio between the dissolved amounts under the crystallization conditions selected, it is possible to cause preferential crystallization of one of the optical isomers which exists in excess.

The crystals of the optically active cysteine derivative (2) obtained in that manner can be recovered by a conventional solid-liquid separation procedure such as pressure filtration, filtration under reduced pressure and centrifugation and, further, the solvent can be removed by atmospheric drying or drying under reduced pressure (vacuum drying).

On the other hand, a method of recovering the product cysteine derivative (2) without any extraction procedure comprises recovering the above cysteine derivative (2) from an alcohol, water, or a mixture thereof, for example by crystallization, without performing any extraction procedure. The alcohol to be used in this method is not restricted to the alcohol (3) used in carrying out the reaction but may be an alcohol added after reaction and different from the above alcohol (3). Such a method of recovery without performing any extraction procedure is advantageous since the percentage recovery can be readily improved by causing water to exist. For that purpose, the solubility and/or the mixing ratio between water and a solvent such as an alcohol in the step of recovery is controlled by admixing water with the reaction mixture, distilling off under reduced pressure an arbitrarily selected amount of the above alcohol (3) and/or some other solvent in the reaction mixture, or by further adding water.

Depending on the species and amount of the solvent used in the reaction, such as an alcohol, the recovery is preferably carried out, according to need, by a combination of water content adjustment, solvent removal by distillation, concentration, and cooling.

In increasing the water content in the reaction mixture when the reaction solvent used is a highly water-miscible monohydric alcohol containing 1 to 4 carbon atoms, such as methanol, the water content in the system in the step of recovery is generally not less than 10% by weight, preferably not less than about 20% by weight, more preferably not less than about 30% by weight, based on the total amount of the above alcohol (3) and water, from the improved recovery and improved operability viewpoint.

The reaction mixture contains not only the desired product cysteine derivative (2) but also the strong acid, or the byproduct hydrogen halide and sulfur dioxide when a thionyl halide is used, and is thus in a state containing very strongly acidic substances. It is not always necessary to remove these strongly acidic substances prior to the step of recovery. When they are removed, however, they can be removed by the method mentioned herein above. Such removal is effected by neutralization and, when the neutralization is carried out in the manner mentioned herein above, the precipitation can be effected while allowing the water used together with the base and the water formed to coexist as they are. In the presence of water, the contaminants such as the unreacted raw materials and salts formed therefrom generally show high solubilities while the desired product cysteine derivative (2) shows a low solubility. Therefore, there is a tendency toward efficient precipitation of the cysteine derivative (2) with high quality.

When, in the cysteine derivative (2), $R^0$ is a hydrogen atom, $R^1$ is a urethane type protective group, $R^2$ is a phenyl group and $R^3$ is an alkyl group containing 1 to 4 carbon atoms, the above cysteine derivative (2) can favorably be crystallized out by using, as the crystallization solvent, a monohydric alcohol containing 1 to 4 carbon atoms or a mixed solvent composed of a monohydric alcohol containing 1 to 4 carbon atoms and water under acidic to weakly basic conditions. Particularly when the above cysteine derivative (2) is N-benzyloxycarbonyl-S-phenylcysteine methyl ester ($R^0$=hydrogen atom, $R^1$=benzyloxycarbonyl, $R^2$=phenyl, $R^3$=methyl), the use, as the crystallization solvent, of methanol or a mixed solvent composed of methanol and water under acidic to weakly basic conditions is particularly preferred. In the case of a mixed solvent composed of methanol and water, the content of water in the system, which is recommendable from the viewpoint of impurity removal, is generally less than about 10% by weight, preferably less than about 5% by weight, more preferably less than about 1% by weight, based on the total amount of methanol and water. It is judicious to use methanol singly as the crystallization solvent, since, in that case, simplification of the crystallization procedure and/or facilitation of recovery and reuse of the solvent, in addition to efficient removal of said impurity, can be attempted.

When a mixed solvent composed of a monohydric alcohol containing 1 to 4 carbon atoms and water is used as the crystallization solvent, the condition concerning the water content in the system which is adequate for the purpose in the practical procedure may be determined taking into consideration the recovery rate, the operability and the effect of removing each impurity.

The above method of crystallization is applicable also to the crystallization of the product obtained by a process other than the production process of the present invention. In particular when a low grade of the cysteine derivative (2) containing impurities such as the optical isomer and a dehydroalanine derivative is subjected to the above-mentioned method of crystallization, said dehydroalanine derivative being represented by the general formula (5):

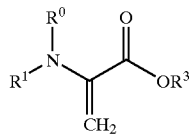

(5)

wherein $R^0$ represents a hydrogen atom, $R^1$ represents a urethane type amino-protecting group and $R^3$ represents an alkyl group containing 1 to 4 carbon atoms, and being hardly formed as byproducts in the production process of the present invention, the impurities mentioned above can be removed efficiently, hence the above method of crystallization is effective also as a method of purifying the cysteine derivative (2). For example, the content of the impurity optical isomer can be reduced to 2% or less, preferably to 1% or less, and the dehydroalanine derivative (5) can be almost completely eliminated.

For the effects of the above method of purification to be produced to its maximum, when the cysteine derivative (2) contains its optical isomer as an impurity, it is judicious to adjust the crystallization conditions such as the species of solvents, the mixing ratio therebetween and the recovery temperature in the step of crystallization so that the relative equilibrium solubility (equilibrium ratio between the amounts dissolved) in the crystallization mixture between the desired optically active cysteine derivative (2) and its optical isomer may become lower than the optical purity of the cysteine derivative before crystallization, to thereby cause preferential crystallization of the desired optically active cysteine derivative (2), which exists in excess, while efficiently removing the impurity optical isomer into the mother liquor. By this measure, it is possible to obtain the optically active cysteine derivative (2) with a percent existence of the desired optical isomer of not less than 98%, preferably not less than 99%.

In other words, the relative solubility in the solution between the optically active cysteine derivative (2) and its optical isomer has a constant value (namely, there is an equilibrium ratio between the amounts dissolved) depending on the crystallization conditions selected, such as the solvent species and the mixing ratio between the solvents constituting the mixed solvent, independently of the optical purity of the cysteine derivative used in the crystallization step, so that when the optical purity of the cysteine derivative used in the crystallization step is higher than the equilibrium ratio between the dissolved amounts under the crystallization conditions selected, it is possible to cause preferential crystallization of one of the optical isomers which exists in excess.

The temperature for the above crystallization is not restricted but generally is from the solidifying temperature to about 60° C.

In particular, for recovering the cysteine derivatives (2) as crystals, it is judicious to adjust the concentration of the same in the step of recovering to a slurry concentration of not higher than 30% (w/v), preferably not higher than 20% (w/v) by adjusting the amount of water to be admixed, the amount of the solvent to be distilled off and the recovery temperature, among others, to thereby maintain the fluidity in the step of crystallization and to obtain a crystallization mixture showing good slurry properties by slowly cooling or slowly admixing water, for instance.

In the above step of crystallization, generally known methods of crystallization such as cooling crystallization or by concentrating crystallization can be employed. The so-called reactive crystallization is also considered possible which comprises causing the cysteine derivative (2) formed with the progress of the reaction to crystallize out successively by adjusting the conditions such as the temperature, concentration and other factors for the reaction.

The cysteine derivative (2) that has crystallized out can be collected by a conventional solid-liquid separation procedure such as pressure filtration, filtration under reduced pressure and centrifugation and, further, the solvent can be removed by atmospheric drying or drying under reduced pressure (vacuum drying).

The present invention thus provides an industrially excellent method by which the side reactions are prevented and the cysteine derivative (2) is obtained in a simple and efficient manner. The yield of the cysteine derivative (2) can be expected to be not less than 90%, preferably almost quantitative. A particular advantage of the present invention is that the racemization can favorably be prevented. The degree of racemization, namely the decrease in optical purity

[in the case of L form, for instance, 100%×L form/(L form+D form)], can be suppressed to 2% or less, preferably 1% or less.

BEST MODES FOR CARRYING OUT THE INVENTION

The following examples illustrate the present invention in further detail. They are, however, by no means limitative of the scope of the invention.

In the examples, the optical purity [100%×L-form/(L form+D form)] of the N-benzyloxycarbonyl-S-phenyl-L-cysteine used was 99.6%. The optical purity [100%×L-form/(L form+D form)] of the product N-benzyloxycarbonyl-S-phenyl-L-cysteine methyl ester was determined using a HPLC column for separating optical isomers (CHIRALPAK AD, product of Daicel Chemical Industry). The yield and purity of N-benzyloxycarbonyl-S-phenyl-L-cysteine were given for the sum of the L-form and D-form.

EXAMPLE 1

In a nitrogen atmosphere, 1,500 ml of methanol was added to 300.9 g of N-benzyloxycarbonyl-S-phenyl-L-cysteine and 8.64 g of p-toluenesulfonic acid monohydrate, and the reaction was allowed to proceed under reflux. After 6 hours of reaction, the mixture was cooled to about 40° C., and the pH was adjusted to 5.5 by adding 82 ml of a 5% (by weight) aqueous solution of sodium hydrogen carbonate. Then, the methanol was replaced with toluene at about 40° C., to give 1152.7 g of a toluene-substituted reaction mixture. Then, 200 ml of a 20% (by weight) aqueous solution of sodium chloride was added at 45 to 50° C., and the pH was adjusted to 7.8 with 23 ml of a 5% (by weight) aqueous solution of sodium hydrogen carbonate. After separation of the aqueous phase, the organic phase was washed with two 200-ml portions of a 20% (by weight) aqueous solution of sodium chloride at 45 to 50° C., to give 1130.6 g of a toluene solution, This toluene solution contained 309.8 g (concentration: 27.4% by weight) of N-benzyloxycarbonyl-S-phenyl-L-cysteine methyl ester; the yield was 99% and the optical purity was 99.7%.

Further, from 1129.1 g of the toluene solution containing 309.4 g of N-benzyloxycarbonyl-S-phenyl-L-cysteine methyl ester, removal of the toluene by distillation was started at an inside temperature of 60 to 70° C. and, finally, at an internal pressure of 20 mm Hg and an inside temperature of 68° C., there was obtained 317.2 g of an oil containing N-benzyloxycarbonyl-S-phenyl-L-cysteine methyl ester.

Prior to the above toluene removal by distillation, melting point determination was carried out and it was confirmed that crystals of the N-benzyloxycarbonyl-S-phenyl-L-cysteine methyl ester had a melting point of 65° C. Referring to the melting point 65° C., a temperature of 65 to 70° C. was employed as the operation temperature. In the subsequent examples, the operation temperature was selected in the same manner.

To the above oil was added 298.6 g of tetrahydrofuran, to give 615.8 g of a tetrahydrofuran solution of N-benzyloxycarbonyl-S-phenyl-L-cysteine methyl ester. This tetrahydrofuran solution contained 309.0 g (concentration: 50.2% by weight) of N-benzyloxycarbonyl-S-phenyl-L-cysteine methyl ester; the yield was 100%, the optical purity was 99.7% and the amount of residual toluene was 1.9 g (concentration: 0.3% by weight). The formation of N-benzyloxy-carbonyldehydroalanine methyl ester was not observed.

REFERENCE EXAMPLE 1

About 150 g of the reaction mixture after 6 hours of reaction as obtained by the same procedure as in Example 1 and having an N-benzyloxycarbonyl-S-phenyl-L-cysteine methyl ester concentration of 20.5% by weight was adjusted to pH 6, 10, 11 or 12 by adding an aqueous solution of sodium hydrogen carbonate or an aqueous solution of sodium hydroxide, and each mixture was maintained at 40° C. for 1 hour with stirring. Each reaction mixture was subjected to substitution of the methanol for toluene in the same manner as in Example 1 at about 40° C. and 20 ml of a 20% (by weight) aqueous solution of sodium chloride was added to the toluene-substituted reaction mixture. After separation of the aqueous phase, the organic phase was washed with two 20-ml portions of a 20% (by weight) aqueous solution of sodium chloride at 45 to 50° C., and the toluene solution obtained was assayed for the optical purity of N-benzyloxycarbonyl-S-phenyl-L-cysteine methyl ester and the yield of N-benzyloxycarbonyldehydroalanine methyl ester. The results thus obtained are shown in Table 1.

TABLE 1

| pH | Optical purity (%) | Yield of N-benzyloxycarbonyl-dehydroalanine methyl ester (mol %) |
| --- | --- | --- |
| 6  | 99.6 | Not detected |
| 10 | 99.6 | 0.2 |
| 11 | 80.4 | 2.6 |
| 12 | 73.1 | 2.1 |

EXAMPLE 2

In a nitrogen atmosphere, a solution prepared by admixing 458 mg of concentrated sulfuric acid with 10 ml of methanol was added to 30.03 g of N-benzyloxycarbonyl-S-phenyl-L-cysteine and 140 ml of methanol, and the reaction was allowed to proceed under reflux. After 10 hours of reaction, the mixture was cooled to room temperature and the pH was adjusted to 5.5 by adding 8 ml of a 5% (by weight) aqueous solution of sodium hydrogen carbonate. Then, the methanol was replaced with toluene at about 50° C., to give 116 g of a toluene-substituted reaction mixture. The mixture was then washed with two 40-ml portions of a 10% (by weight) aqueous solution of sodium sulfate at 45 to 50° C. to give 113.5 g of a toluene solution. This toluene solution contained 30.7 g (concentration: 27.1% by weight) of N-benzyloxycarbonyl-S-phenyl-L-cysteine methyl ester; the yield was 98% and the optical purity was 99.6%.

Further, removal of the toluene by distillation was started from 112.0 g of the toluene solution containing 30.3 g of N-benzyloxycarbonyl-S-phenyl-L-cysteine methyl ester at an inside temperature of 60 to 70° C. and, finally, at an internal pressure of 20 mm Hg and an inside temperature of 67° C., there was obtained 31.5 g of an oil containing N-benzyloxycarbonyl-S-phenyl-L-cysteine methyl ester. To this was added 30.0 g of tetrahydrofuran, to give 61.5 g of a tetrahydrofuran solution of N-benzyloxycarbonyl-S-phenyl-L-cysteine methyl ester. This tetrahydrofuran solution contained 30.3 g (concentration: 49.2% by weight) of N-benzyloxycarbonyl-S-phenyl-L-cysteine methyl ester; the yield was 100%, the optical purity was 99.6% and the amount of residual toluene was 0.2 g (concentration: 0.3% by weight). The formation of N-benzyloxycarbonyldehydroalanine methyl ester was not detected.

EXAMPLE 3

In a nitrogen atmosphere, 11.8 g of thionyl chloride was added to 47 ml of methanol over 1 hour with stirring at −3 to 0° C., and the reaction was further allowed to proceed for 1 hour at the same temperature (solution A). Separately, 30.02 g of N-benzyloxycarbonyl-S-phenyl-L-cysteine was admixed with 103 ml of methanol (solution B). Solution A was added to solution B over 20 minutes at about 25° C. and then the reaction was allowed to proceed at the same temperature for 2 hours. Thereafter, the mixture was warmed to about 50° C. While effecting degassing and distilling off the methanol under reduced pressure at an internal pressure of 100 mm Hg, toluene was added, to give 121.5 g of a toluene solution. This solution was adjusted to pH 8.1 by adding 20 ml of a 10% (by weight) aqueous solution of sodium chloride and 10 ml of a 5% (by weight) aqueous solution of sodium hydrogen carbonate at 40° C. After separation of the aqueous phase, the organic phase was washed with two 20-ml portions of a 10% (by weight) aqueous solution of sodium chloride at 40 to 45° C., to give 123.0 g of a toluene solution. This toluene solution contained 30.7 g (concentration: 24.9% by weight) of N-benzyloxycarbonyl-S-phenyl-L-cysteine methyl ester; the yield was 98% and the optical purity was 99.6%. The formation of N-benzyloxycarbonyldehydroalanine methyl ester was not detected.

EXAMPLE 4/REFERENCE EXAMPLE 2

In a nitrogen atmosphere, 150 ml of methanol was added to 30.01 g of N-benzyloxycarbonyl-S-phenyl-L-cysteine and 864 mg of p-toluenesulfonic acid monohydrate, and the reaction was allowed to proceed under reflux. After 6 reaction hours, the mixture was cooled to about 50° C., and the pH was adjusted to 5.5 by adding 8 ml of a 5% (by weight) aqueous solution of sodium hydrogen carbonate. Then, the methanol was replaced with toluene at about 50° C., to give 103.87 g of a toluene-substituted reaction mixture containing 30.97 g (concentration: 29.8% by weight; yield: 99%; optical purity: 99.7%) of N-benzyloxycarbonyl-S-phenyl-L-cysteine methyl ester (Example 4). Then, 15 ml of pure water was added to this toluene-substituted reaction mixture at room temperature, and the mixture was stirred for 15 minutes and then allowed to stand, whereupon the aqueous phase formed a large number of droplets, which remained dispersed or settled in the organic phase but did not unite with one another. This procedure thus failed to form two layers, namely the upper and lower layers, separable from each other, hence to enable phase separation (Reference Example 2).

To a mixture of the above toluene solution and water was added 335 mg (corresponding to a concentration in water of 6.3% by weight) of sodium chloride, and the mixture was stirred for 15 minutes at 45 to 50° C. and then allowed to stand, whereupon the organic and aqueous phases rapidly formed two separable layers, upper and lower layers; phase separation thus became possible (Example 4).

EXAMPLE 5/REFERENCE EXAMPLE 3

Toluene removal by distillation was started from 254.4 g of a toluene solution obtained in the same manner as in Example 1 and containing 49.4 g (concentration: 19.4% by weight; optical purity: 99.7%) of N-benzyloxycarbonyl-S-phenyl-L-cysteine methyl ester at an inside temperature of 60 to 70° C. and, finally, 50.6 g of an oil containing N-benzyloxycarbonyl-S-phenyl-L-cysteine methyl ester was obtained at an internal pressure of 20 mm Hg and an inside temperature of 70° C. To this was promptly added 43.4 g of tetrahydrofuran, to give 93.9 g of a tetrahydrofuran solution of N-benzyloxycarbonyl-S-phenyl-L-cysteine methyl ester. This tetrahydrofuran solution contained 49.3 g (concentration: 52.5% by weight) of N-benzyloxycarbonyl-S-phenyl-L-cysteine methyl ester; the yield was 100%, the optical purity was 99.7% and the amount of residual toluene was 0.7 g (concentration: 0.3% by weight) (Example 5).

Separately, from 254.4 g of the same toluene solution containing 49.4 g (concentration: 19.4% by weight; optical purity: 99.7%) of N-benzyloxycarbonyl-S-phenyl-L-cysteine methyl ester was distilled off the toluene at an inside temperature of 40° C., whereupon stirring became more and more difficult and, when the concentration of N-benzyloxycarbonyl-S-phenyl-L-cysteine methyl ester reached 78.1% by weight, the stirrer stopped (Reference Example 3).

EXAMPLE 6

A toluene solution (58.3 g) obtained in the same manner as in Example 1 and containing 13.0 g (concentration: 22.3% by weight) of N-benzyloxycarbonyl-S-phenyl-L-cysteine methyl ester was concentrated under reduced pressure at an inside temperature of 40° C. to finally give a toluene solution with an N-benzyloxycarbonyl-S-phenyl-L-cysteine methyl ester concentration of 65% by weight. Dropwise addition of hexane to this solution was started at 40° C. with stirring while the mixture was slowly cooled to 20° C., to thereby cause precipitation of white crystals. After addition of a total amount of 130 ml of hexane, the mixture was cooled to -10° C. and further stirred for 3 hours. Then, the crystals were recovered by filtration and dried under reduced pressure (1 to 30 mm Hg, 20 to 40° C., 10 hours). The crystals obtained weighed 12.5g (yield95%), the purity was 99.5%by weight and the optical purity was 99.8%.

The thus-obtained N-benzyloxycarbonyl-S-phenyl-L-cysteine methyl ester gave the following 400 MHz nuclear magnetic resonance spectrum (CDCl$_3$; internal standard: TMS) δ: 3.36–3.45 (2H, m), 3.53 (3H, s), 4.61–4.65 (1H, m), 5.03–5.10 (2H, ABq, J=12.5 Hz), 5.60–5.62 (1H, b), 7.17–7.45 (10H, m)

REFERENCE EXAMPLE 4

In a nitrogen atmosphere and at room temperature, 125 mg of sodium hydride (content: 67.4%) was added to a solution composed of 399 mg of thiophenol and 3 ml of N,N-dimethylformamide, and the mixture was stirred for 30 minutes, and the resulting solution was maintained at 20° C. To the solution was added 971 mg of N-benzyloxycarbonyl-O-mesyl-L-serine methyl ester, followed by washing the residue thereof into the solution with 2 ml of N,N-dimethylformamide. After the lapse of 2 hours, a minimum amount of the reaction mixture was taken out and analyzed by HPLC; the starting material N-benzyloxycarbonyl-O-mesyl-L-serine methyl ester was no more detected, the ratio between the total number of moles of N-benzyloxycarbonyl-S-phenyl-L-cysteine methyl ester and N-benzyloxycarbonyl-S-phenyl-D-cysteine methyl ester and the number of moles of N-benzyloxycarbonyldehydroalanine methyl ester was 89:11, and the optical purity was 87.7%. After a total 20 hours of reaction, the reaction mixture obtained was analyzed by HPLC. As a result, the yield of N-benzyloxycarbonyl-S-phenyl-L-cysteine methyl ester was 696 mg (69% yield) and the optical purity was 80.1%. The yield of N-benzyloxycarbonyldehydroalanine methyl ester was 2.2%.

REFERENCE EXAMPLE 5

In a nitrogen atmosphere and at room temperature, 52 ml of 1 N aqueous sodium hydride and 32 ml of distilled water were added to 5.87 g of thiophenol with stirring and the resulting 30 mixture was stirred for 30 minutes. Then, 0.74 g of benzyltributylammonium chloride was added, and the solution was cooled to about 10° C. To the solution was added, all at one, a solution composed of 13.9 g of N-carbobenzoxy-O-mesyl-L-serine and 60 ml of ethyl acetate, with the residual portion being washed with 10 ml of ethyl acetate. After the reaction was allowed to proceed at 10° C. for 10 hours, the temperature was raised to room temperature over 2 hours. To this reaction mixture were added 70 ml of toluene and 8.2 g (corresponding to a concentration in water of 10% by weight) of sodium chloride for one extraction procedure, which was carried out at 45–50° C. After separation of the aqueous layer, the extract was washed with two 50-ml portions of a 10% (by weight) aqueous solution of sodium chloride at 45 to 50° C. to give 136.8 g of an extract. This extract contained 13.8 g of N-carbobenzoxy-S-phenyl-L-cysteine methyl ester and 0.2 g of N-benzyloxycarbonyldehydroalanine methyl ester; the yield was 95% and the optical purity was 94.5%.

EXAMPLE 7

In a nitrogen atmosphere, a solution prepared by admixing 65 mg of concentrated sulfuric acid with 10 ml of methanol was added to 20.08 g of N-benzyloxycarbonyl-S-phenyl-L-cysteine and 40 ml of methanol, and the reaction was allowed to proceed under reflux. After 50 hours of reaction, the mixture was cooled to about 25° C. The pH of the solution was 1.2. Then, the solution was cooled to −15° C. over 3 hours with vigorous stirring, and the resulting crystalline precipitate was filtered off and dried under reduced pressure to give 19.22 g (yield: 91%) of white crystals. The purity of these crystals of N-benzyloxycarbonyl-S-phenyl-L-cysteine methyl ester was 99.1% by weight and the optical purity was 99.9%. The formation of N-benzyloxycarbonyldehydroalanine methyl ester was not detected.

EXAMPLE 8

In a nitrogen atmosphere, 150 ml of methanol was added to 30.09 g of N-benzyloxycarbonyl-S-phenyl-L-cysteine and 864 mg of p-toluenesulfonic acid monohydrate, and the reaction was allowed to proceed under reflux. After 6 hours of reaction, the mixture was cooled to about 50° C. and adjusted to pH 8.0 by adding 10 ml of a 5% (by weight) aqueous solution of sodium hydrogen carbonate. Then, 110 ml of pure water was added dropwise over 3 hours with vigorous stirring at about 50° C., the resulting mixture was cooled to 5° C., and the resulting precipitate crystals were filtered off and washed in sequence with a mixed solution composed of 50 ml of methanol and 50 ml of pure water and with 100 ml of pure water and then dried under reduced pressure to give 30.89 g (yield: 98%) of white crystals. With these crystals, the purity of N-benzyloxycarbonyl-S-phenyl-L-cysteine methyl ester was 99.7% by weight and the optical purity was 99.8%. The formation of N-benzyloxycarbonyldehydroalanine methyl ester was not detected.

The thus-obtained N-benzyloxycarbonyl-S-phenyl-L-cysteine methyl ester gave the following 400 MHz nuclear magnetic resonance spectrum (CDCl$_3$; internal standard: TMS) δ: 3.36–3.45 (2H, m), 3.53 (3H, ), 4.61–4.65 (1H, m), 5.03–5.10 (2H, ABq, J=12.5 Hz), 5.60–5.62 (1H, b), 7.17–7.45 (10H, m).

EXAMPLE 9

In a nitrogen atmosphere, a solution prepared by admixing 458 ml of concentrated sulfuric acid with 10 ml of methanol was added to 30.03 g of N-benzyloxycarbonyl-S-phenyl-L-cysteine and 140 ml of methanol, and the reaction was allowed to proceed under reflux. After 6 hours of reaction, the mixture was cooled to about 50° C. and adjusted to pH 8.0 by adding 15 ml of a 5% (by weight) aqueous solution of sodium hydrogen carbonate. Then, 105 ml of pure water was added dropwise over 3 hours with vigorous stirring at about 50° C., the resulting mixture was cooled to 5° C., and the precipitate crystals were then filtered off, washed in sequence with a mixed solution composed of 50 ml of methanol and 50 ml of pure water and with 100 ml of pure water, and dried under reduced pressure to give 30.67 g (yield: 98%) of white crystals, With these crystals, the purity of N-benzyloxycarbonyl-S-phenyl-L-cysteine methyl ester was 99.6% by weight and the optical purity was 99.8%. The formation of N-benzyloxycarbonyldehydroalanine methyl ester was not detected.

EXAMPLE 10

In a nitrogen atmosphere, 11.8 g of thionyl chloride was added to 47 ml of methanol over 1 hour with stirring at 3 to 6° C., and the reaction was further allowed to proceed for 1 hour at the same temperature (solution A). Separately, in a nitrogen atmosphere, 30.02 g of N-benzyloxycarbonyl-S-phenyl-L-cysteine was admixed with 103 ml of methanol (solution B). Solution A was added to solution B over 30 minutes at about 25° C. and then the reaction was allowed to proceed at the same temperature for 2 hours to give 155.2 g of a methanolic solution. This solution was warmed to about 50° C. and adjusted to pH 8.0 by adding 70 ml of a 10% (by weight) aqueous solution of sodium hydroxide. Then, 57 ml of pure water was added dropwise over 3 hours with vigorous stirring at about 50° C., the mixture was cooled to 5° C., and the resulting precipitate crystals were filtered off, washed in sequence with a mixed solution composed of 50 ml of methanol and 50 ml of pure water and with 100 ml of pure water and then dried under reduced pressure to give 30.91 g (yield: 98%) of white crystals. With these crystals, the purity of N-benzyloxycarbonyl-S-phenyl-L-cysteine methyl ester was 99.6% and the optical purity was 99.8%. The formation of N-benzyloxycarbonyldehydroalanine methyl ester was not detected.

EXAMPLE 11

In a nitrogen atmosphere, 5 ml of methanol and 150 ml of toluene were added to 30.0 g of N-benzyloxycarbonyl-S-phenyl-L-cysteine and 864 mg of p-toluenesulfonic acid monohydrate, and the reaction was allowed to proceed under reflux. While the byproduct water was removed by azeotropic distillation and the toluene phase of the distillate was returned to the reaction system, the reaction was allowed to proceed for 6 hours. The mixture was then cooled to about 40° C. and adjusted to pH 5.5 by adding 8 ml of a 5% (by weight) aqueous solution of sodium hydrogen carbonate. Then, the methanol was replaced with toluene at about 40° C. to give 115.3 g of a toluene-substituted reaction mixture. Thereto was then added 20 ml of a 20% (by weight) aqueous solution of sodium chloride at 45 to 50° C., and the pH was adjusted to 7.9 with 2.3 ml of a 5% (by weight) aqueous solution of sodium hydrogen carbonate. After separation of the aqueous phase, the organic phase was washed with two 20-ml portions of a 20% (by weight) aqueous solution of sodium chloride at 45 to 50° C., to give 113.2 g of a toluene solution. This toluene solution contained 30.4 g (concentration: 26.9% by weight) of N-benzyloxycarbonyl-S-phenyl-L-cysteine methyl ester; the yield was 97% and the optical purity was 99.6%.

Further, from 112.1 g of the toluene solution containing 30.2 g of N-benzyloxycarbonyl-S-phenyl-L-cysteine methyl ester, removal of the toluene by distillation was started at an inside temperature of 60 to 70° C. and, finally, at an internal pressure of 20 mm Hg and an inside temperature of 68° C., there was obtained 30.7 g of an oil containing N-benzyloxycarbonyl-S-phenyl-L-cysteine methyl ester. To this was added 29.6 g of tetrahydrofuran, to give 60.9 g of a tetrahydrofuran solution of N-benzyloxycarbonyl-S-phenyl-L-cysteine methyl ester. This tetrahydrofuran solution contained 30.4 g (concentration: 50.4% by weight) of N-benzyloxycarbonyl-S-phenyl-L-cysteine methyl ester; the yield was 100%, the optical purity was 99.6% and the amount of residual toluene was 0.2 g (concentration: 0.3% by weight).

EXAMPLE 12

In a nitrogen atmosphere, 150 ml of methanol was added to 30.0 g of N-benzyloxycarbonyl-S-phenyl-L-cysteine containing 0.1 g (0.4% by weight) of N-benzyl-S-phenylcysteine and 864 mg of p-toluenesulfonic acid monohydrate, and the reaction was allowed to proceed under reflux for 6 hours. The reaction mixture was cooled to about 40° C., to give 149.5 g of a methanol solution. This methanol solution contained 30.9 g (concentration: 20.7% by weight) of N-benzyloxycarbonyl-S-phenyl-L-cysteine methyl ester; the yield was 99% and the optical purity was 99.6%. The solution contained 0.1 g of N-benzyl-S-phenylcysteine but the formation of N-benzyl-S-phenylcysteine methyl ester was not detected.

The methanol solution (147.2 g) containing 30.5 g of N-benzyloxycarbonyl-S-phenyl-L-cysteine methyl ester was adjusted to pH 5.5 by adding 8 ml of a 5% (by weight) aqueous solution of sodium hydrogen carbonate and then the methanol was replaced with toluene at about 40° C., to give 112.8 g of a toluene-substituted reaction mixture. Then, 10 ml of a 10% (by weight) aqueous solution of sodium chloride was added at 45 to 50° C., the pH was adjusted to 0.3 with 35% (by weight) hydrochloric acid, and washing was repeated three times under acidic conditions. Further, 10 ml of a 10% (by weight) aqueous solution of sodium chloride was added at 45 to 50° C. and the pH was adjusted to 7.9 with 19.8 ml of a 5% (by weight) aqueous solution of sodium hydrogen carbonate. After separating the aqueous phase, the organic phase was washed with two 20-ml portions of a 20% (by weight) aqueous solution of sodium chloride at 45 to 50° C., to give 111.5 g of a toluene solution. This toluene solution contained 30.4 g (concentration: 27.3% by weight) of N-benzyloxycarbonyl-S-phenyl-L-cysteine methyl ester; the yield was 100% and the optical purity was 99.6%. The contamination with N-benzyl-S-phenylcysteine or N-benzyl-S-phenylcysteine methyl ester was not detected.

Further, from 109.1 g of the toluene solution containing 29.8 g of N-benzyloxycarbonyl-S-phenyl-L-cysteine methyl ester, removal of the toluene by distillation was started at an inside temperature of 60 to 70° C. and, finally, at an internal pressure of 20 mm Hg and an inside temperature of 68° C., there was obtained 30.3 g of an oil containing N-benzyloxycarbonyl-S-phenyl-L-cysteine methyl ester. To this was added 29.6 g of tetrahydrofuran, to give 59.9 g of a tetrahydrofuran solution of N-benzyloxycarbonyl-S-phenyl-L-cysteine methyl ester. This tetrahydrofuran solution contained 29.8 g (concentration: 49.7% by weight) of N-benzyloxycarbonyl-S-phenyl-L-cysteine methyl ester; the yield was 100%, the optical purity was 99.6% and the amount of residual toluene was 0.2 g (concentration: 0.3% by weight).

EXAMPLE 13

From 67.2 g of the extract obtained in Reference Example 5 and containing 6.78 g (optical purity: 94.5%) of N-benzyloxycarbonyl-S-phenyl-L-cysteine methyl ester and 0.11 g of N-benzyloxycarbonyldehydroalanine methyl ester, removal of the ethyl acetate and toluene by distillation was started at 200 mm Hg and an inside temperature of about 40° C., and, finally at 20 mm Hg and an inside temperature of about 68° C., there was obtained 6.92 g of an oil containing N-benzyloxycarbonyl-S-phenyl-L-cysteine methyl ester. To this was added promptly 30 ml of toluene, to give 32.81 g of a toluene solution. This toluene solution contained 6.76 g of N-benzyloxycarbonyl-S-phenyl-L-cysteine methyl ester and 0.11 g of N-benzyloxy-carbonyldehydroalanine methyl ester; the yield was 100% and the optical purity was 94.5%.

A 32.33 g portion of this toluene solution (containing 6.66 g of N-benzyloxycarbonyl-S-phenyl-L-cysteine methyl ester and 0.11 g of N-benzyloxycarbonyldehydroalanine methyl ester) was cooled to 25° C. and then 30 ml of hexane was added dropwise over 3 hours with vigorous stirring, followed by further cooling to 5° C. The resulting precipitate crystals were filtered off, the wet crystals obtained were washed with 10 ml of hexane and then dried under reduced pressure (1 to 30 mm Hg, 20 to 40° C., 10 hours) to give 5.43 g (yield: 81%) of white crystals. With these crystals, the purity of N-benzyloxycarbonyl-S-phenyl-L-cysteine methyl ester was 99.5% by weight and the optical purity was 98.7%. The contamination with N-benzyloxycarbonyldehydroalanine methyl ester was not detected.

REFERENCE EXAMPLE 6

One gram each of N-benzyloxycarbonyl-S-phenyl-L-cysteine methyl ester samples differing in optical purity was dissolved in 5 mL of toluene, and 5 mL of hexane was added at about 25° C. with stirring. After thorough crystallization, the optical purity of the soluble fraction was determined. The results thus obtained are shown in Table 2.

TABLE 2

| Initial optical Purity (%) | Optical purity of soluble fraction (%) |
| --- | --- |
| 90.5 | 79.3 |
| 81.9 | 79.9 |
| 63.8 | 79.2 |

Regardless of the initial optical purity, the optical purity values of the N-benzyloxycarbonyl-S-phenyl-L-cysteine methyl ester samples dissolved showed substantially the same value (79 to 80%).

EXAMPLE 14

From 67.0 g of the extract obtained in Reference Example 5 and containing 6.76 g (optical purity: 94.5%) of N-benzyloxycarbonyl-S-phenyl-L-cysteine methyl ester and 0.11 g of N-benzyloxycarbonyldehydroalanine methyl ester, removal of the ethyl acetate and toluene by distillation was started at 200 mm Hg and an inside temperature of about 40° C., and, finally, at 20 mm Hg and an inside temperature of about 68° C., there was obtained 6.95 g of an oil containing N-benzyloxycarbonyl-S-phenyl-L-cysteine methyl ester. To this was added promptly 16 ml of methanol, to give 19.71 g of a methanol solution. This methanol solution contained 6.74 g of N-benzyloxycarbonyl-S-phenyl-L-cysteine methyl ester and 0.11 g of N-benzyloxy-carbonyldehydroalanine methyl ester; the yield was 100% and the optical purity was 94.5%.

A 18.66 g portion of this methanol solution (containing 6.38 g of N-benzyloxycarbonyl-S-phenyl-L-cysteine methyl ester and 0.11 g of N-benzyloxycarbonyldehydroalanine methyl ester) was cooled to 5° C. over 3 hours with vigorous stirring, and the resulting crystals were filtered off. The wet crystals obtained were washed in sequence with a mixed solution composed of 10 ml of methanol and 10 ml of pure water and with 20 ml of pure water and then dried under reduced pressure to give 4.55 g (yield: 71%) of white crystals. With these crystals, the purity of N-benzyloxycarbonyl-S-phenyl-L-cysteine methyl ester was 99.0% by weight and the optical purity was 99.7%. Contamination with N-benzyloxycarbonyldehydroalanine methyl ester was not detected.

REFERENCE EXAMPLE 7

One gram each of N-benzyloxycarbonyl-S-phenyl-L-cysteine methyl ester samples differing in optical purity was added to 15 mL of methanol and dissolution was effected at about 25° C. with stirring. This solution was cooled and, after thorough crystallization, the optical purity of the soluble fraction was determined. The results thus obtained are shown in Table 3.

TABLE 3

| Initial optical Purity (%) | Optical purity of soluble fraction (%) |
| --- | --- |
| 90.5 | 86.3 |
| 81.9 | 85.3 |

Regardless of the initial optical purity, the optical purity values of the N-benzyloxycarbonyl-S-phenyl-L-cysteine methyl ester samples dissolved showed substantially the same value (85 to 87%).

INDUSTRIAL APPLICABILITY

The production process of the present invention, which is as mentioned above, is economically advantageous, achieves high production efficiency on a commercial scale as well, and enables production of the optically active cysteine derivatives with particularly high optical purity and good quality.

What is claimed is:

1. A process for producing an optically active cysteine derivative represented by the general formula (2):

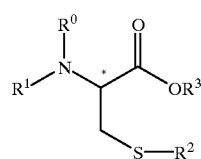

(2)

wherein $R^1$ represents an amino-protecting group of the urethane or acyl type, $R^0$ represents a hydrogen atom or, taken together with the above $R^1$, an amino-protecting group, $R^2$ represents a univalent organic group selected from the group consisting of a substituted or unsubstituted alkyl group containing 1 to 7 carbon atoms, a substituted or unsubstituted aryl group containing 6 to 10 carbon atoms and a substituted or unsubstituted aralkyl group containing 7 to 10 carbon atoms, $R^3$ represents a univalent organic group capable of functioning as an ester-type carboxyl-protecting group by its being included in the structure represented by —COOR$^3$ and * represents the position of an asymmetric carbon atom, which comprises reacting a D-form or L-form optically active amino acid derivative represented by the general formula (1):

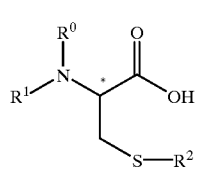

(1)

wherein $R^0$, $R^1$, $R^2$ and * are defined above, with an alcohol represented by the general formula (3):

$$R^3OH \qquad (3)$$

wherein $R^3$ is as defined above, and a strong acid and/or a thionyl halide to synthesize a D-form or l-form optically active cysteine derivative represented by said general formula (2), extracting the optically active cysteine derivative of the general formula (2) from the reaction mixture using an extraction solvent to recover an organic phase containing said optically active cysteine derivative (2), wherein addition of an inorganic salt and/or warming treatment is applied to thereby cause separation of said organic phase and an aqueous phase, and recovering said optically active cysteine derivative (2) from said organic phase the procedural series from said reaction to said recovery being carried out under a condition such that the medium contracting the above optically active cysteine derivative (2) is within the range from acidic to weakly basic to thereby recover the above optically active cysteine derivative (2) from the reaction mixture while suppressing the decomposition that racemization thereof.

2. The process for producing an optically active cysteine derivative according to claim 1, wherein the decrease in optical purity during the procedural series from reaction to recovery is not more than 2%.

3. The process for producing an optically active cysteine derivative according to claim 1, wherein the strong acid remaining in the reaction mixture and/or hydrogen halide and sulfur dioxide formed as a byproduct are/is eliminated by neutralization using a base.

4. The process for producing an optically active cysteine derivative according to claim 1, wherein said extraction of the optically active cysteine derivative of the general formula (2) using an extraction solvent is carried out from the reaction mixture as such or from the reaction mixture after reduction of the reaction solvent content.

5. The process for producing an optically active cysteine derivative according to claim 1,
wherein at least one of aromatic hydrocarbons and acetate esters is used as the extraction solvent.

6. The process for producing an optically active cysteine derivative according to claim 1,
wherein, in concentrating the organic phase containing the optically active cysteine derivative or at a temperature not lower than the melting temperature of the concentrate comprising said optically active cysteine derivative as the main component, to thereby recover said optically active cysteine derivative in the form of an oily substance.

7. The process for producing an optically active cysteine derivative according to claim 6,
wherein a solvent is further added to the optically active cysteine derivative of the general formula (2) as obtainable in the form of an oily substance, to give a solution of said optically active cysteine derivative.

8. The process for producing an optically active cysteine derivative according to claim 1,
wherein, in causing the optically active cysteine derivative of the general formula (2) to precipitate from the organic phase containing said optically active cysteine derivative, adding an aliphatic hydrocarbon as a poor solvent to said organic phase or a concentrate of said organic phase, and recovering the optically active cysteine derivative.

9. The process for producing an optically active cysteine derivative according to claim 8,
wherein the aliphatic hydrocarbon is hexane.

10. The process for producing an optically active cysteine derivative according to claim 1,
wherein, when a compound represented by the general formula (4):

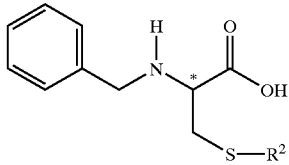

(4)

wherein $R^2$ and * are as defined above, coexists, as a contaminant, in the optically active amino acid derivative of the general formula (1), $R^1$ being benzyloxycarbonyl, said compound of the general formula (4) is caused to remain substantially unreacted in the reaction step.

11. The process for producing an optically active cysteine derivative according to claim 10,
wherein the compound of the general formula (4), which remains unreacted, is removed from the reaction mixture.

12. The process for producing an optically active cysteine derivative according to claim 11,
wherein the compound of the general formula (4) is removed by filtration and/or a phase separation procedure comprising extraction and washing.

13. The process for producing an optically active cysteine derivative according to claim 12,
wherein the phase separation procedure comprising extraction and washing is carried out under an acidic condition with addition of an inorganic salt and/or warming treatment, to thereby causing the compound of the general formula (4) to transfer to the aqueous phase.

14. The process for producing an optically active cysteine derivative according to claim 1,
wherein, in general formula (1), $R^2$ is a phenyl group.

15. The process for producing an optically active cysteine derivative according to claim 14,
wherein, in general formula (1), $R^1$ is a urethane-type protecting group.

16. The process for producing an optically active cysteine derivative according to claim 15,
wherein the urethane-type protecting group is an aralkyloxycarbonyl group or a lower alkoxycarbonyl group.

17. The process for producing an optically active cysteine derivative according to claim 16,
wherein said urethane-type protecting group is benzyloxycarbonyl, tert-butoxycarbonyl, methoxycarbonyl or ethoxycarbonyl.

18. The process for producing an optically active cysteine derivative according to claim 17,
wherein the urethane-type protecting group is benzyloxycarbonyl.

19. The process for producing an optically active cysteine derivative according to claim 10,
wherein, in general formula (1), $R^2$ is a phenyl group.

20. The process for producing an optically active cysteine derivative according to claim 14,
wherein, in general formula (2), $R^3$ is a lower alkyl group containing 1 to 4 carbon atoms.

21. The process for producing an optically active cysteine derivative according to claim 20,
wherein the lower alkyl group containing 1 to 4 carbon atoms is methyl.

* * * * *